United States Patent [19]

Indig

[11] Patent Number: 5,432,319
[45] Date of Patent: Jul. 11, 1995

[54] FURNACE FOR HEAT TREATMENT OF DENTAL PRODUCTS IN AN INERT ATMOSPHERE

[76] Inventor: Baruch Indig, 8 Tevrski Street, Tel-Aviv, Israel

[21] Appl. No.: 27,017

[22] Filed: Mar. 5, 1993

[30] Foreign Application Priority Data

Mar. 19, 1992 [IL] Israel ...................................... 101306

[51] Int. Cl.⁶ .............................................. F27B 5/14
[52] U.S. Cl. .................................. 219/390; 219/402; 373/109; 118/725; 432/121
[58] Field of Search ............................... 373/109–112, 373/118, 137, 140–141, 145; 219/390, 393, 400, 416, 411, 391, 402, 405; 118/715, 725, 729; 432/121, 124, 241; 126/92 R

[56] References Cited

U.S. PATENT DOCUMENTS

| | | | |
|---|---|---|---|
| 4,412,812 | 11/1983 | Sadowski et al. | 432/121 |
| 4,753,192 | 6/1988 | Goldsmith et al. | 118/725 |
| 4,760,244 | 7/1988 | Hokynar | 219/390 |
| 4,828,490 | 5/1989 | Indig | 432/124 |
| 4,954,685 | 9/1990 | Kumagai et al. | 219/390 |
| 5,131,842 | 7/1992 | Miyazaki et al. | 432/241 |
| 5,163,416 | 11/1992 | Schultz et al. | 126/92 R |

Primary Examiner—Bruce A. Reynolds
Assistant Examiner—Tu Hoang
Attorney, Agent, or Firm—Hana Dolezalova

[57] ABSTRACT

A high temperature furnace for heat treatment of various products, and for sintering. One of the uses is for preparing dental products such as dental crowns, bridges, implants and the like. The main component of the furnace is a cup-shaped quartz vessel, with a curved roof section, and which has a wide flange at its open end. There is provided a heating coil, applied to the vessel, and heat insulating means and heat measuring means indicating the temperature inside the vessel. There is provided a tube leading to the outside which can be used for establishing a vacuum in the vessel or for providing in the vessel or for providing in the vessel an atmosphere of any desired gas or gas mixture. There is provided a base through which there can be raised and lowered a worktable. The flange of the vessel rests on O-rings which provide a hermetic seal, and which are not subjected to an excessive temperature due to the width to the width of the flange of the vessel. There is provided an efficient thermal insulation and means for highly accurate heating of the vessel.

8 Claims, 1 Drawing Sheet

FURNACE FOR HEAT TREATMENT OF DENTAL PRODUCTS IN AN INERT ATMOSPHERE

FIELD OF THE INVENTION

The invention relates to a novel type of furnace which is useful for the heat treatment of various materials in a controlled atmosphere. The furnaces are of special use for heat treatment in an inert atmosphere. One of the preferred applications is in the production of dental products, such as crowns, bridges and the like, and especially in the production of products from starting materials which have to be sintered in an inert atmosphere.

BACKGROUND OF THE INVENTION

There are known various types of furnaces, including specific ones for use in the production of dental products. One of the problems is the provision of a suitable atmosphere. Another is the problem of heat conductivity. One specific type of furnace is described in Israel Patent No. 79109, which corresponds to U.S. Pat. No. 4,828,490.

The present invention overcomes various drawbacks of existing furnaces.

SUMMARY OF THE INVENTION

The invention relates to a high-temperature furnace, adapted for the high temperature treatment of various products and articles, and also for the production of articles by sintering. The furnace makes possible the operation of the active volume of the furnace in an inert atmosphere or under vacuum.

DETAILED DESCRIPTION OF THE PREFERRED EMBODIMENTS

Figure 1:
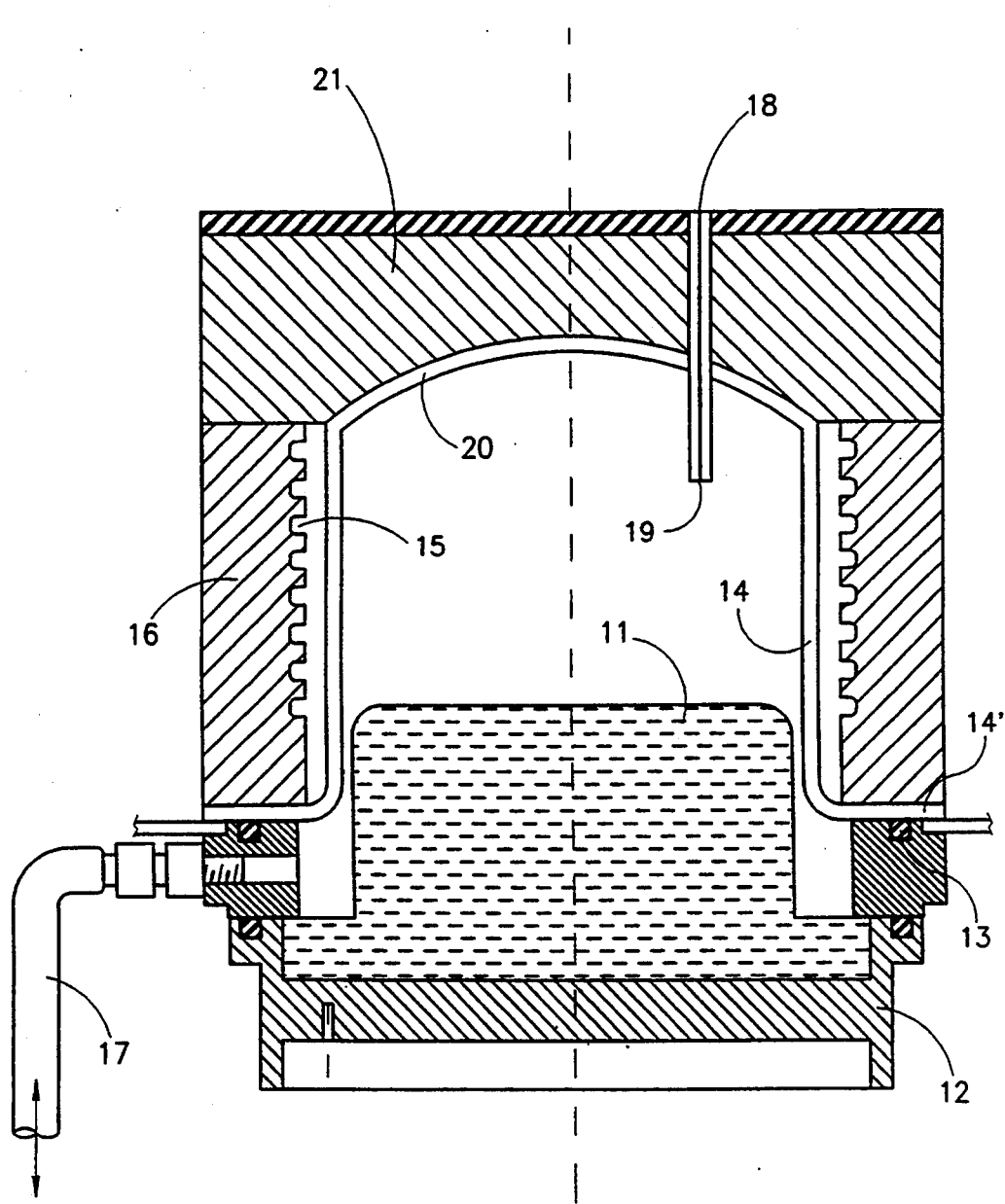
FIG. 1 is an elevational cross-sectional view of a furnace.

The furnace is based on the use of an inner transparent or translucent flanged cup-shaped vessel, connected with means for establishing a vacuum or an inert gaseous atmosphere, which is provided with an external coil of resistance wire for the controlled heating of the interior of the vessel. A workpiece, supported by a movable table is introduced into the vessel. Furthermore there are provided an efficient thermal insulation and heat measuring thermocouple. Especially suitable is the use of ceramic fibers as thermal insulation. Especially advantageous results were attained with a model using an inverted flanged quartz vessel, provided with an inlet for a stream of inert gas (or gas mixture) or for the evacuation of the interior of the vessel, and another connection with the outside for use with temperature measuring means, such as a thermocouple or the like.

The vessel is surrounded by a suitable thermal insulation layer 21 such as chamotte, ceramic fiber layer or the like. The vessel is supported by a suitable support, and sealed hermetically when required by a silicon O-ring. A working table is provided which may be lowered and raised, so as to reach into the vessel. This too can be made of ceramic fiber.

The invention is described by way of illustration only with reference to the enclosed schematical drawing, which is not according to scale, and which is an elevational cross-sectional view through a furnace of the invention (FIG. 1).

As shown in FIG. 1, the furnace comprises a support Table 11, which is made of a block of ceramic fiber, and which is supported by the metal base 12. This support is provided with a seal, a silicon O-ring 13, on which there rests the lower flange of the inverted cup-shaped quartz vessel 14, on which there is provided a resistance wire coil 15, which in turn is surrounded by thermal ceramic fiber insulation 16.

The cup-shaped vessel is provided with an inlet tube 18 which serves for the insertion of a thermocouple or the like. This is fused to the upper, curved part of this vessel.

There is provided a further inlet tube 17 which passes through the lower part of the device, below the O-ring 13 and which is in communication with the interior of vessel 14, and through which this vessel can be evacuated, or flushed with an inert gas and thus there can be provided an inert atmosphere in vessel 14.

It is a very important feature of the present invention that the vessel 14 is provided a wide flange 14': only such a wide flange permits adequate thermal separation between the heated cup-shaped part of vessel 14 and such flange, so that this flange (rim) does not reach too high a temperature, and this makes possible the use of an O-ring 13 for hermetic sealing of the interior of the vessel. When the tube 17 is connected with a vacuum source, there is established an airtight seal between the flange of the vessel 14 and the support base 12. The heating spiral 15 is connected with a variable power supply, thus making possible an accurate temperature control, which is monitored by means of thermocouple 19. One of the main advantages of the present invention is the provision of the flanged quartz bell, the flange 14' of which extends for a sufficient distance from the heated body of said vessel 14 in order to remain at a manageable temperature, and allowing the use of the O-ring 13. The support table 11, which is used to support the work piece in the furnace, can be raised and lowered.

A furnace was constructed with a vessel of about 95 mm inner diameter, height of about 100 mm and curved roof, with a wall thickness of about 1.5 mm. The furnace was tested with material requiring sintering in the temperature range or about 300° C. to about 1150° C., for a period of about 30 minutes. Work was carried out in an argon atmosphere, which was established by flushing twice the interior with argon and by in-between evacuation. Temperature can be held at a desired level with variations in the 1 to 3 degree range.

I claim:

1. A high temperature furnace for high temperature treatment and sintering of products in a controlled inert atmosphere, said furnace comprising:
   a flanged transparent or translucent inverted cup-shaped container with a flange part, a cylindrical part and a curved roof section wherein said container is made of a temperature resistant quartz material;
   a resistance wire heating coil surrounding an exterior of said cylindrical part of the cup-shaped container for heating a container interior to a temperature up to 1150° C.;
   a thermal insulation surrounding said heating coil, said flange part, and the curved roof section of the container for maintaining said temperature during the heat treatment and sintering;

a thermocouple for measuring temperature;
inlet tubes;
a base structure;
an O-ring seal placed between said flange part of the container and between the base structure of the furnace for establishing a hermetic seal between the base structure and said container; and
a movable support for supporting the workpiece entry into the container, said movable support fitting into the container interior and supporting the workpiece during the high temperature treatment and sintering in an inert atmosphere.

2. The furnace according to claim 1 wherein the container is an inverted, flanged quartz vessel provided with said inlet tubes including a first inlet tube for introduction of the thermocouple into the interior of the vessel.

3. The furnace according to claim 2, wherein said inlet tubes further include a second inlet tube is entered through the base structure as a device connecting the interior of the container with the exterior, said device used for evacuating the container and for introducing a inert gas or mixture thereof.

4. The furnace according to claim 3, wherein the O-ring seal is made of a temperature resistant silicon rubber.

5. The furnace according to claim 4, wherein the thermal insulation comprises a layer of a ceramic fiber.

6. The furnace according to claim 5, wherein the inert gas is argon.

7. A high temperature furnace for high temperature treatment and sintering of dental products in a controlled atmosphere, said furnace comprising:
a flanged transparent or translucent inverted cup-shaped container with a flange part, a cylindrical part, and a curved roof section wherein said container is made of a temperature resistant quartz material;
a resistance wire heating coil surrounding an exterior of said cylindrical part of the cup-shaped container for heating a container interior to a temperature up to 1150° C.;
a thermal insulation surrounding said heating coil, said flange part, and the curved roof section of the container for maintaining said temperature during the heat treatment and sintering;
a thermocouple for measuring temperature;
inlet tubes;
a base structure;
an O-ring seal placed between said flange part of the container and between the base structure of the furnace for establishing a hermetic seal between the base structure and said container; and
a movable support for supporting said dental products entry into the container, means for moving said movable support into the container interior for supporting said dental products during the high temperature treatment and sintering in an inert atmosphere.

8. A method for heat treatment and sintering of dental products in a controlled inert atmosphere, comprising steps:
(a) introducing a dental product into a high temperature furnace comprising:
a flanged transparent or translucent inverted cup-shaped container with a flange part, a cylindrical part, and a curved roof section wherein said container is made of a temperature resistant quartz material;
a resistance wire heating coil surrounding an exterior of said cylindrical part of the cup-shaped container for heating a container interior to a temperature up to 1150° C.;
a thermal insulation surrounding said heating coil, said flange part, and the curved roof section of the container for maintaining said temperature during the heat treatment and sintering;
a thermocouple for measuring temperature;
inlet tubes;
a base structure;
an O-ring seal placed between said flange part of the container and between the base structure of the furnace for establishing a hermetic seal between the base structure and said container; and
a movable support for supporting said dental products entry into the container, said movable support fitting into the container interior and supporting the workpiece during the high temperature treatment and sintering in an inert atmosphere;
(b) establishing an internal vacuum within the container interior by airtight sealing the container to the base structure by O-ring seal upon evacuation of the container and insertion of an inert gas;
(c) repeating step (b) at least two times;
(d) heating to and maintaining a container interior at a temperature in a range from about 300° C. to about 1150° C. for a period of about 30 minutes;
(e) terminating the heating and vacuum.

* * * * *